United States Patent [19]

Romaniuk et al.

[11] Patent Number: 4,785,825
[45] Date of Patent: Nov. 22, 1988

[54] SAFETY BIOPSY FORCEPS

[75] Inventors: Paul Romaniuk; Jürgen Speder; Hans-Peter Dübel, all of Berlin; Siegfried Müller, Jena, all of German Democratic Rep.

[73] Assignee: Humboldt—Universitaet zu Berlin, Berlin, German Democratic Rep.

[21] Appl. No.: 154,505

[22] Filed: Feb. 4, 1988

Related U.S. Application Data

[63] Continuation of Ser. No. 53,570, May 21, 1987, abandoned, which is a continuation of Ser. No. 810,468, Dec. 18, 1985, abandoned.

[30] Foreign Application Priority Data

Dec. 28, 1984 [DD] German Democratic Rep. ................................. 2720554

[51] Int. Cl.⁴ .............................................. A61B 10/00
[52] U.S. Cl. ..................................... 128/751; 128/321
[58] Field of Search ................................ 128/321–324, 128/749–758

[56] References Cited

U.S. PATENT DOCUMENTS

| | | | |
|---|---|---|---|
| 439,910 | 11/1890 | Truax | 128/321 |
| 3,840,003 | 10/1974 | Komiya | 128/751 |
| 4,522,206 | 6/1985 | Whipple et al. | 128/752 |

FOREIGN PATENT DOCUMENTS 165285  11/1963  U.S.S.R. ............................. 128/749

Primary Examiner—Edward M. Coven
Assistant Examiner—Randy Citrin
Attorney, Agent, or Firm—Jordan and Hamburg

[57] ABSTRACT

Safety biopsy forceps, in particular for infants, comprise operating forceps, a flexible shaft, a pulling element, as well as a head with cutting- and/or grasping elements, of which at least one element is moveable by means of the pulling element, provided with a head with cutting- and/or grasping element which is detachably fastened on the flexible shaft. The flexible shaft is detachably fastened to the operating forceps and the pulling element to the operating forceps. The pulling element is adjustable for the setting of the cutting- and/or grasping elements and the setting of the force of the cutting process and can also be locked in after the adjustment. The cutting- and/or grasping elements are provided at the joint with a recess which prevents tissue from becoming lodge during closing of the elements.

2 Claims, 2 Drawing Sheets

SAFETY BIOPSY FORCEPS

This application is a continuation of application Ser. No. 053,570 filed May 21, 1987, now abandoned which is a continuation of application Ser. No. 810,468 filed Dec. 18, 1985 now abandoned.

BACKGROUND OF THE INVENTION AND RELATED ART STATEMENT

The invention relates to safety biopsy forceps which are suitable in particular for infants for all ventricles of the heart and for the biopsy of the left ventricle of the heart of adults.

Biopsy forceps are conventionally known for collecting specimens of mucous from
  the mouth and the throat
  the respiratory tract (trachea and bronchial system)
  the stomach canal and intestinal tract
  the hollow organs of the kidneys
  the bladder and
  the uterus.

There are also known biopsy forceps for collecting specimens of heart tissue. They are preferably inserted via plastic catheters up to in front of the cardiac wall. Then the spoons are opened and pressed towards the heart tissue. The forceps are pulled shut and the spoons thereby grasp the tissue and cut out a specimen thereof which is pulled out through the catheter. The conventional prior art biopsy forceps are only suitable for the right half of the heart having a soft tissue. Therefore, it allows a relatively slight collection of specimen of tissue thereof. Problems arise when it is used in the left ventricle of the heart, because the tissue thereof is less segmented and smoother. The spoon forceps slip off and do not grasp.

There are also diseases which are accompanied by a thickening and/or hardening of the cardiac wall, whereby a satisfactory removal of the tissue is not possible with the conventionally known biopsy forceps.

The conventional prior art forceps are designed as disposable instruments and can be used only once. Because the wires shift during operation, it is no longer possible to attain a definite spoon position when the forceps are used a second time. This can already occur, if during the first application, there is not removed any tissue, or only an insuffient amount of tissue. In this case, a second try is very risky, and the forceps have to be taken out and replaced by a new instrument. Otherwise, during the second try, it is possible that the wide open initial position is no longer attained, which would pose the risk of perforating the cardiac wall, or at least could result in an insufficient specimen collection.

Another disadvantage of the conventionally known disposable instruments consists in that blood enters via the spiral which is not impermeable to fluid whereas the Bowden pulling means cannot be cleaned, because the head of the instrument is tightly fastened to the flexible pulling means. Also the handles of the conventionally known forceps are undetachably fastened to the flexible Bowden pulling means and cannot be cleaned.

In addition to the mentioned disadvantages, these disposable instruments are also highly uneconomical, not only with respect to material usage, but also due to the resulting costs thereof.

Furthermore, another great disadvantage is that they are not adaptable to various tissues, which can cause faulty biopsies.

The object of the invention is to overcome the disadvantages of the conventionally known forceps not only with respect to material usage and costs thereof, but also with respect to their lacking adaptability.

SUMMARY OF THE INVENTION

The present invention has the object to provide biopsy forceps which can be applied to a broader field of application. They should be suitable for infants for all ventricles of the heart and they should also be suitable for the left ventricles of the hearts of adults. Furthermore, they should be adaptable to various kinds of tissues, they should be easy to clean and should be adjustable with respect to the force of their action.

According to the invention, this object is solved by biopsy forceps comprising operating forceps, a flexible shaft, a pulling element, as well as a head with cutting elements and/or grasping elements, whereby at least one cutting element and/or grasping element is movable by means of the pulling element, whereby the head is detachably fastened to the cutting elements and/or grasping elements on the flexible shaft, the flexible shaft being detachably fastened on the operating forceps, operating forceps, as well as the pulling element being detachably fastened on the operating forceps and being adjustable for the regulation of the position of the cutting elements and/or the grasping elements and the force of the cutting process, which can be fixed after the adjustment. The cutting elements and/or grasping elements are provided at the joint with a recess, so that during closing of the elements it is not possible that tissue can become jammed, which would hinder the cutting process.

On the flexible shaft there is fixedly arranged a sleeve provided with a thread or a bayonet element which can engage with a complementary thread or bayonet element. Of course, other detachable kinds of connections are also possible, such as, for instance, a snap-in connection, which locks when the head and the sleeve are pressed together and which advantageously can only be non-destructively separated again by means of a suitable tool.

Due to the fact that the individual elements of the instrument can be separated from each other, there are attained many advantages in comparison to the conventional prior art forceps. Besides better material economy and the therewith connected lower costs, the instruments can be designed as an assembly of prefabricated parts, the cutting elements and/or grasping elements can be attached according to the given conditions and the operating forces and opening angles thereof can be adjusted. Furthermore, the forceps according to the invention can be re-used as often as desired and are easy to clean or sterilize.

The invention will hereinafter be explained in greater detail by means of an exemplary embodiment. The accompanying drawings show the following:

DETAILED DESCRIPTION OF A PREFERRED EMBODIMENT

Figure 1:
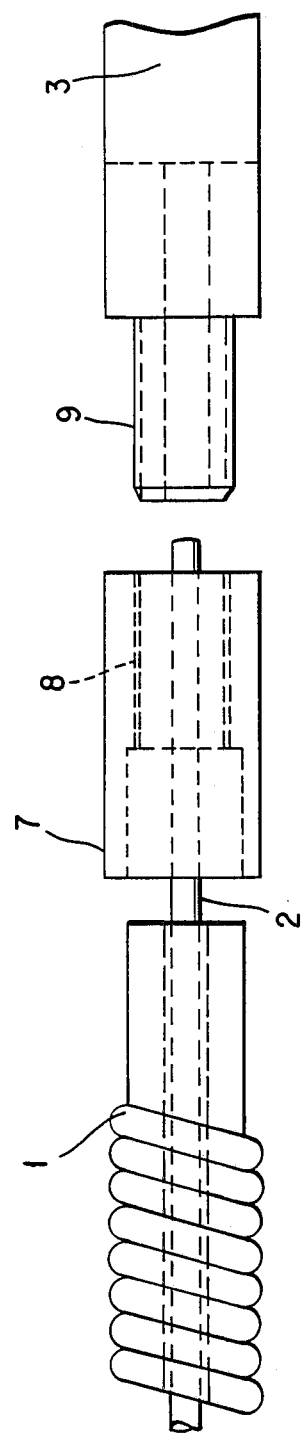
FIG. 1 is a partly schematic exploded side elevation view of a detail of a biopsy forceps of the invention.
Figure 2:
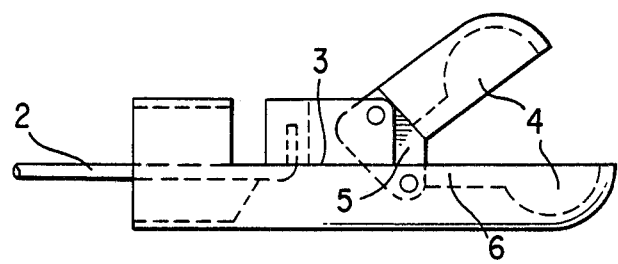
FIG. 2 is a party schematic side elevation view of a biopsy forceps head which may be incorporated in a safety biopsy forceps in accordance with the invention.

FIGS. 1 and 2 show schematically represented parts of a possible form of the biopsy forceps according to the invention consisting of operating forceps (not shown), a flexible shaft 1, a pulling element 2, as well as a head 3 with cutting- and/or grasping elements 4, whereby at least one cutting- and/or grasping element 4 is movable by means of the pulling element 2. The head 3 with the cutting- and/or grasping elements 4 is detachably fastened on the flexible shaft 1. The flexible shaft 1, on the other hand, is detachably fastened to the operating forceps. The pulling element 2 is detachably fastened only to the operating forceps and can be adjusted there by means of conventionally known means for the regulation of the position of the cutting- and/or grasping elements 4 and the force of the cutting process and can be fixed after the adjustment. At the joint 5, the cutting- and/or grasping elements 4 are provided with a recess 6, so that no tissue can become lodged during closing of the elements which would hinder the cutting process.

On a flexible shaft 1 is fixedly arranged a sleeve 7 which is provided with a thread 8 or a bayonet element which can be engaged with a complementary thread 9 or bayonet element at the head 3. Of course, other detachable kinds of connections are also possible, such as a snap-in connection, which locks when the head and the sleeve are pressed together and advantageously can only non-destructively be separated again by means of a suitable tool.

What we claim is:

1. Safety biopsy forceps comprising a head, first and second opposed grasping and/or cutting elements connected to said head, said first opposed element being pivotally mounted to said head at a pivot point adjacent said second opposed element for pivotal movement toward and away from said second opposed element, a hollow flexible shaft, means for detachably fastening together the head and the flexible shaft, an elongated pulling element axially displaceably and coaxially received in the hollow shaft and connected to said first opposed element for acting upon said first opposed element to effect said pivotal movement, said first and second opposed elements each having a free end of spoonlike configuration with mutually facing concavities and each having a recess communicating with said concavity and extending to said pivot point, whereby during actuation of said forceps to effect said pivoted movement to cause tissue to be grasped by and a specimen thereof to be cut out by said opposed elements, said recesses prevent said tissue from jamming between said opposed elements.

2. Safety biopsy forceps according to claim 1, wherein the means for detachably fastening together the head and the flexible shaft comprises an internally threaded hollow sleeve fixed to the flexible shaft and complementary external threads formed on the head antipodal to said opposed elements.

* * * * *